United States Patent
Boggs et al.

(10) Patent No.: US 11,324,350 B1
(45) Date of Patent: May 10, 2022

(54) SECURABLE DELIVERY CONTAINER DEVICE AND METHOD OF USE

(71) Applicants: Charlie Boggs, Marysville, CA (US); Christina Boggs, Marysville, CA (US)

(72) Inventors: Charlie Boggs, Marysville, CA (US); Christina Boggs, Marysville, CA (US)

(*) Notice: Subject to any disclaimer, the term of this patent is extended or adjusted under 35 U.S.C. 154(b) by 0 days.

(21) Appl. No.: 17/233,932

(22) Filed: Apr. 19, 2021

(51) Int. Cl.
A47G 29/14 (2006.01)
A47G 29/30 (2006.01)
B65D 25/54 (2006.01)
G07C 9/00 (2020.01)

(52) U.S. Cl.
CPC ........... *A47G 29/141* (2013.01); *A47G 29/30* (2013.01); *B65D 25/54* (2013.01); *G07C 9/0069* (2013.01)

(58) Field of Classification Search
CPC ...... A47G 29/141; A47G 29/30; B65D 25/54; G07C 9/0069
See application file for complete search history.

(56) References Cited

U.S. PATENT DOCUMENTS

| | | | |
|---|---|---|---|
| 5,971,262 A | 10/1999 | Moore | |
| 6,967,575 B1* | 11/2005 | Dohrmann | G06Q 20/401 340/5.31 |
| 8,358,199 B2* | 1/2013 | Nesling | A47G 29/141 340/568.1 |
| D714,514 S | 9/2014 | Pettit | |
| 9,630,757 B1* | 4/2017 | Capous | A47G 29/20 |
| 10,438,432 B2* | 10/2019 | Espig | G07C 9/00896 |
| 2001/0045449 A1* | 11/2001 | Shannon | G07C 9/21 232/19 |
| 2002/0040564 A1 | 4/2002 | Killingbeck | |
| 2004/0263029 A1 | 12/2004 | Scholefield | |
| 2009/0201198 A1* | 8/2009 | Moudy | G07F 17/13 705/329 |
| 2016/0284149 A1* | 9/2016 | Espig | G07C 9/00182 |
| 2016/0304235 A1 | 10/2016 | Herkenrath | |
| 2017/0251856 A1* | 9/2017 | Schaible | A47G 29/141 |
| 2018/0296016 A1* | 10/2018 | Teoh | A47G 29/20 |

FOREIGN PATENT DOCUMENTS

WO  WO0135358  3/2001

* cited by examiner

*Primary Examiner* — Sisay Yacob (57) ABSTRACT

A securable delivery container device for securing an article during delivery from a sender to a recipient includes a box, which has a top that is open for insertion of an article. A lid hingedly engaged to the box is positioned to selectively close the top. A locking unit, which is engaged to one of the box and the lid, is selectively engageable to the other of the box and the lid when the lid is positioned in a closed configuration. The lid thus is locked to the box. The locking unit requires an instruction to unlock the lid from the box. The instruction is electronically communicable between a sender and an intended recipient of the article. The locking unit secures the article within an interior space defined by the box until delivered to the intended recipient and execution of the instruction.

8 Claims, 7 Drawing Sheets

SECURABLE DELIVERY CONTAINER DEVICE AND METHOD OF USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to delivery containers and more particularly pertains to a new delivery container for securing an article during delivery from a sender to a recipient. The present invention discloses a delivery container comprising a lockable lidded box into which an article can be positioned and secured for delivery, wherein an instruction for unlocking the lid from the box is required to be electronically communicated by a sender to an intended recipient of the article.

(2) Description of Related Art Including Information Disclosed Under 37 CFR 1.97 and 1.98

The prior art relates to delivery containers. Prior art delivery containers may comprise tamper resistant pizza delivery boxes, fixed delivery boxes for receiving packages at delivery sites, and key lockable boxes that are delivered to and secured at delivery sites. What is lacking in the prior art is a delivery container comprising a lockable lidded box into which an article can be positioned and secured for delivery, wherein an instruction for unlocking the lid from the box is required to be electronically communicated by a sender to an intended recipient of the article.

BRIEF SUMMARY OF THE INVENTION

An embodiment of the disclosure meets the needs presented above by generally comprising a box, which has a top that is open so that the box is configured for insertion of an article, such as a meal to be delivered, thereinto. A lid hingedly engaged to the box is positioned to selectively close the top so that the box and the lid define an interior space. A locking unit, which is engaged to one of the box and the lid, is selectively engageable to the other of the box and the lid when the lid is positioned in a closed configuration. The lid thus is locked to the box. The locking unit is configured so that it requires an instruction to unlock the lid from the box. The instruction is electronically communicable between a sender and an intended recipient of the article. The locking unit is configured to secure the article within the interior space until the box is delivered to the intended recipient and the instruction has been executed.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 7 thereof, a new delivery container embodying the principles and concepts of an embodiment of the disclosure and generally designated by the reference numeral 10 will be described.

As best illustrated in FIGS. 1 through 7, the securable delivery container device 10 generally comprises a box 12, which has a top 14 that is open so that the box 12 is configured for insertion of an article thereinto, such as a meal to be delivered. A lid 16 hingedly engaged to the box 12 is positioned to selectively close the top 14 so that the box 12 and the lid 16 define an interior space 18. A handle 20 hingedly engaged to the lid 16 is configured to be grasped in a hand of a user, positioning the user to lift the box 12 and contents thereof.

Figure 6:
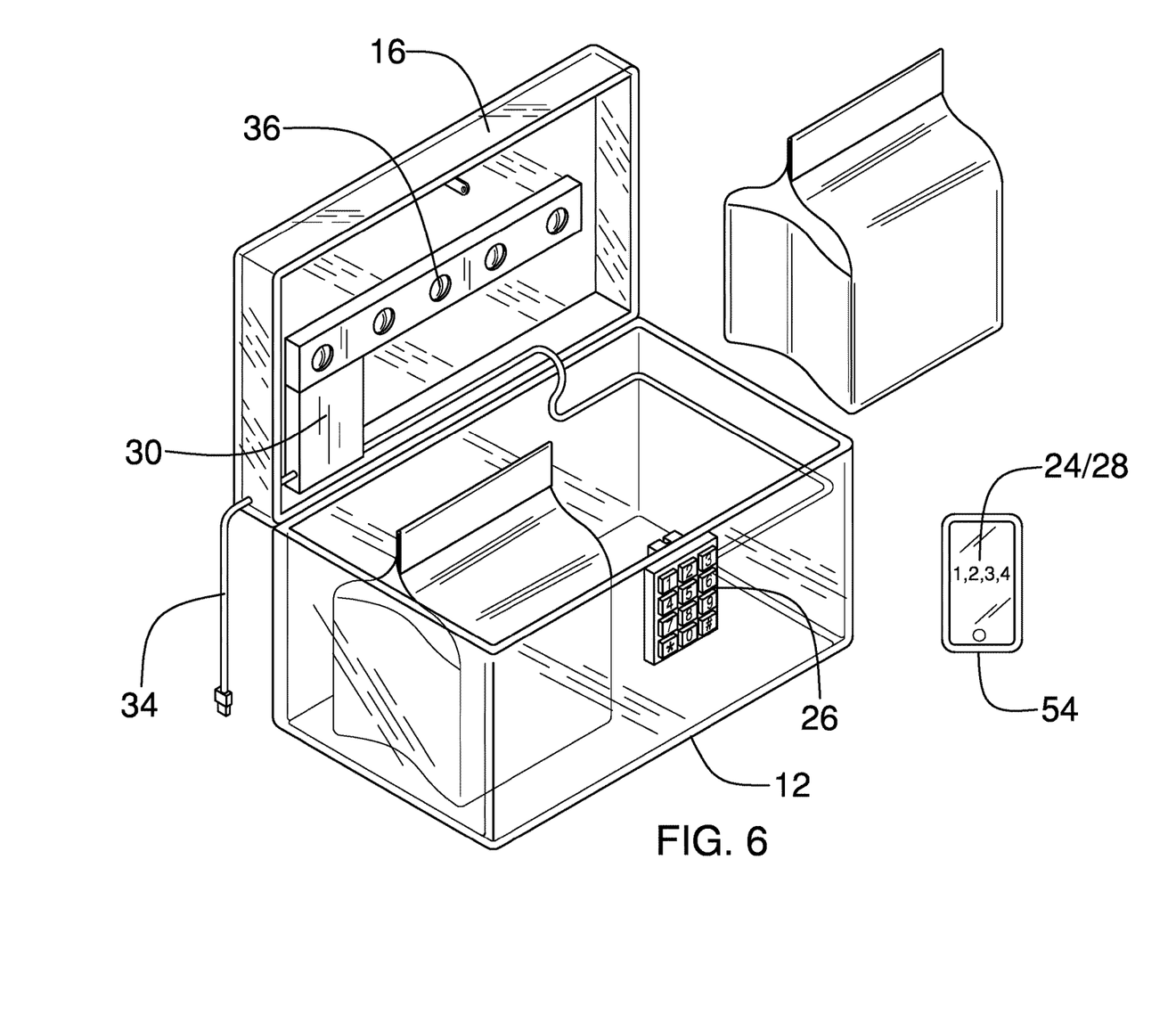
FIG. 6 is an in-use view of an embodiment of the disclosure.

The present invention anticipates the lid 16 being alternatively engaged to the box 12, such as, but not limited to, slidably engaged, removably engaged, and the like. The lid 16 and the box 12 may comprise plastic or other substantially rigid material, such as, but not limited to, metal, wood, and the like. The lid 16 and the box 12 may be substantially transparent, as shown in FIG. 6, or opaque. The present invention also anticipates the box 12 and the lid 16 being insulated.

Figure 1:
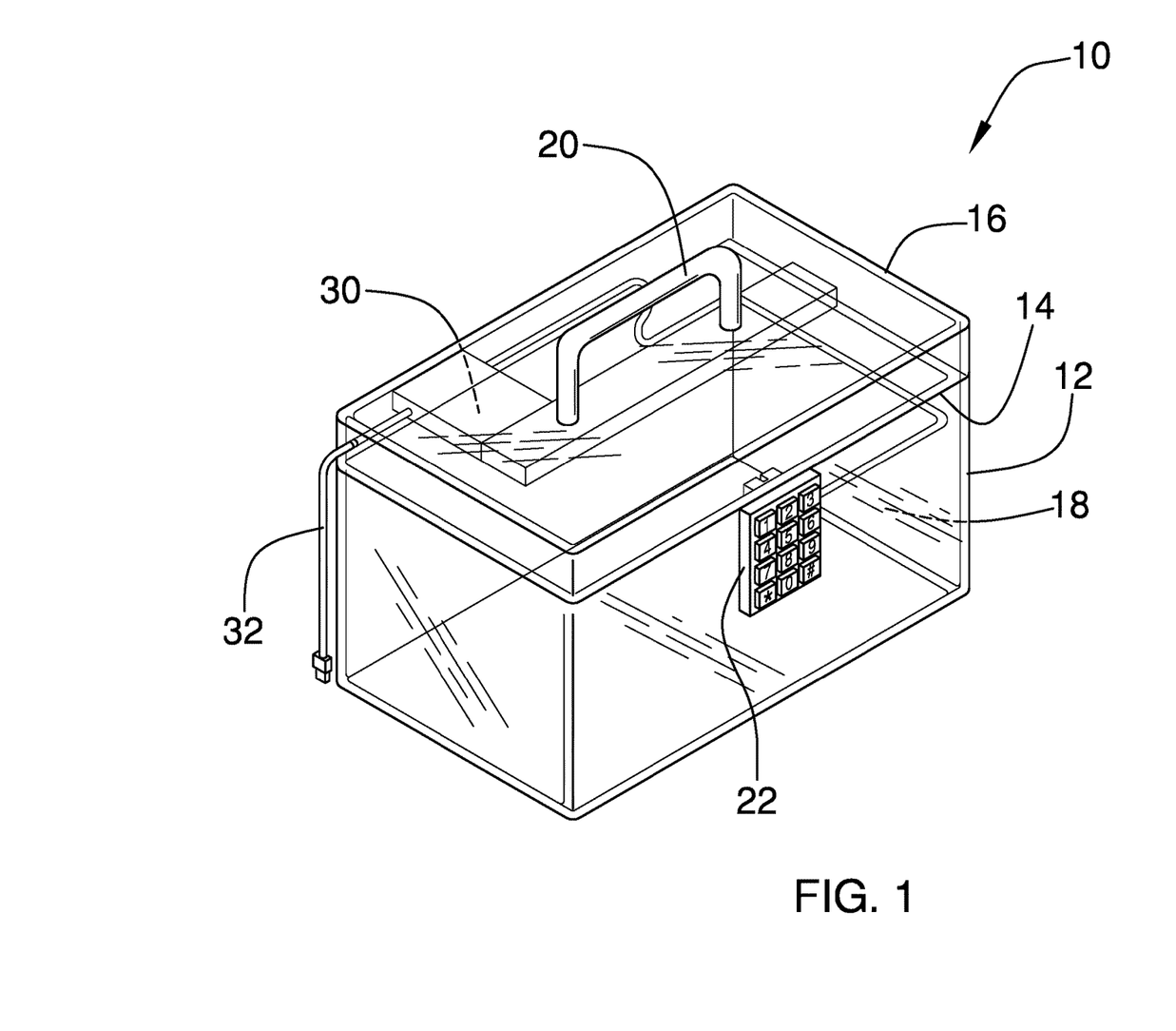
FIG. 1 is an isometric perspective view of a securable delivery container device according to an embodiment of the disclosure.

A locking unit 22, which is engaged to one of the box 12 and the lid 16, is selectively engageable to the other of the box 12 and the lid 16 when the lid 16 is positioned in a closed configuration, as shown in FIG. 1. The lid 16 thus is locked to the box 12. The locking unit 22 is configured so that it requires an instruction 24 to unlock the lid 16 from the box 12. The instruction 24 is electronically communicable between a sender and an intended recipient of the article. The locking unit 22 is configured to secure the article within the interior space 18 until the box 12 is delivered to the intended recipient and the instruction 24 has been executed.

The locking unit 22 may comprise a keypad lock 26, which is configured for entry of the instruction 24 as an alphanumeric code 28, for example, a four digit code communicable to the intended recipient by text messaging, email, voicemail, and the like, which could be received and viewed on an electronic device 54. Entry of the alphanumeric code 28 actuates the locking unit 22 to unlock the lid 16 from the box 12. The present invention anticipates the locking unit 22 comprising other locking means, such as, but not limited to, bar code actuated locks, quick response code actuated locks, and the like.

Figure 2:
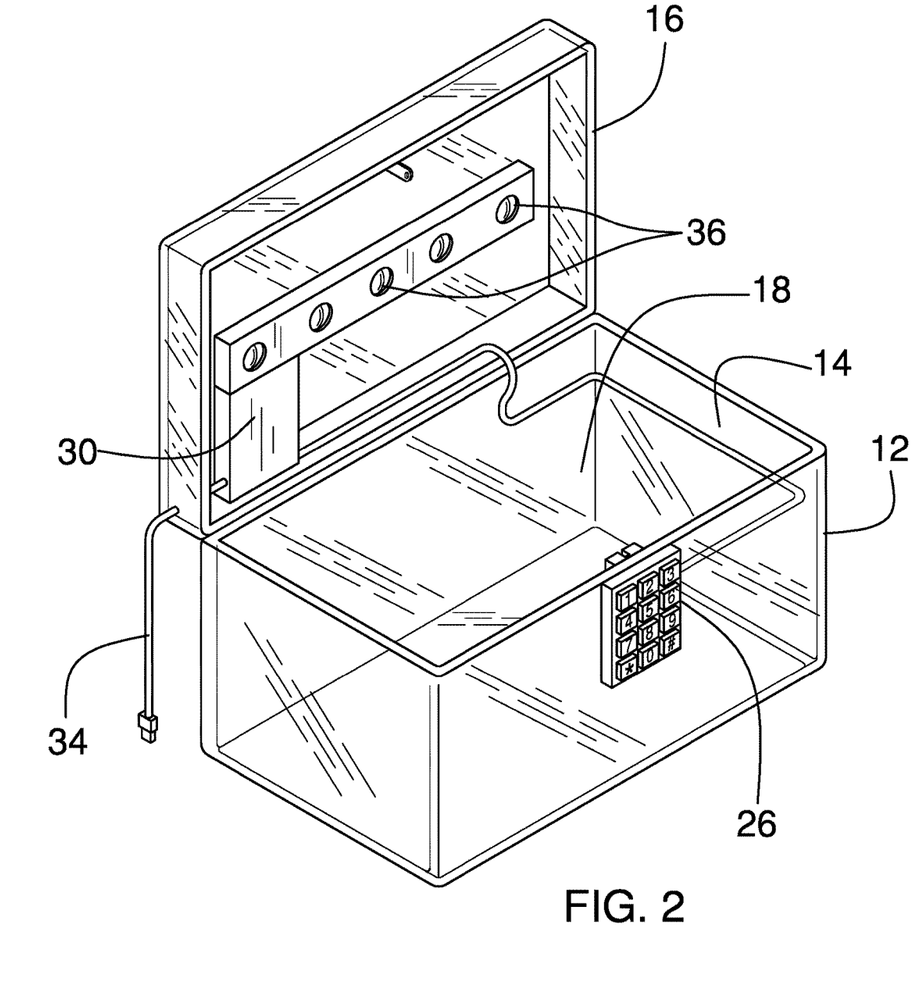
FIG. 2 is an isometric perspective view of an embodiment of the disclosure.
Figure 3:
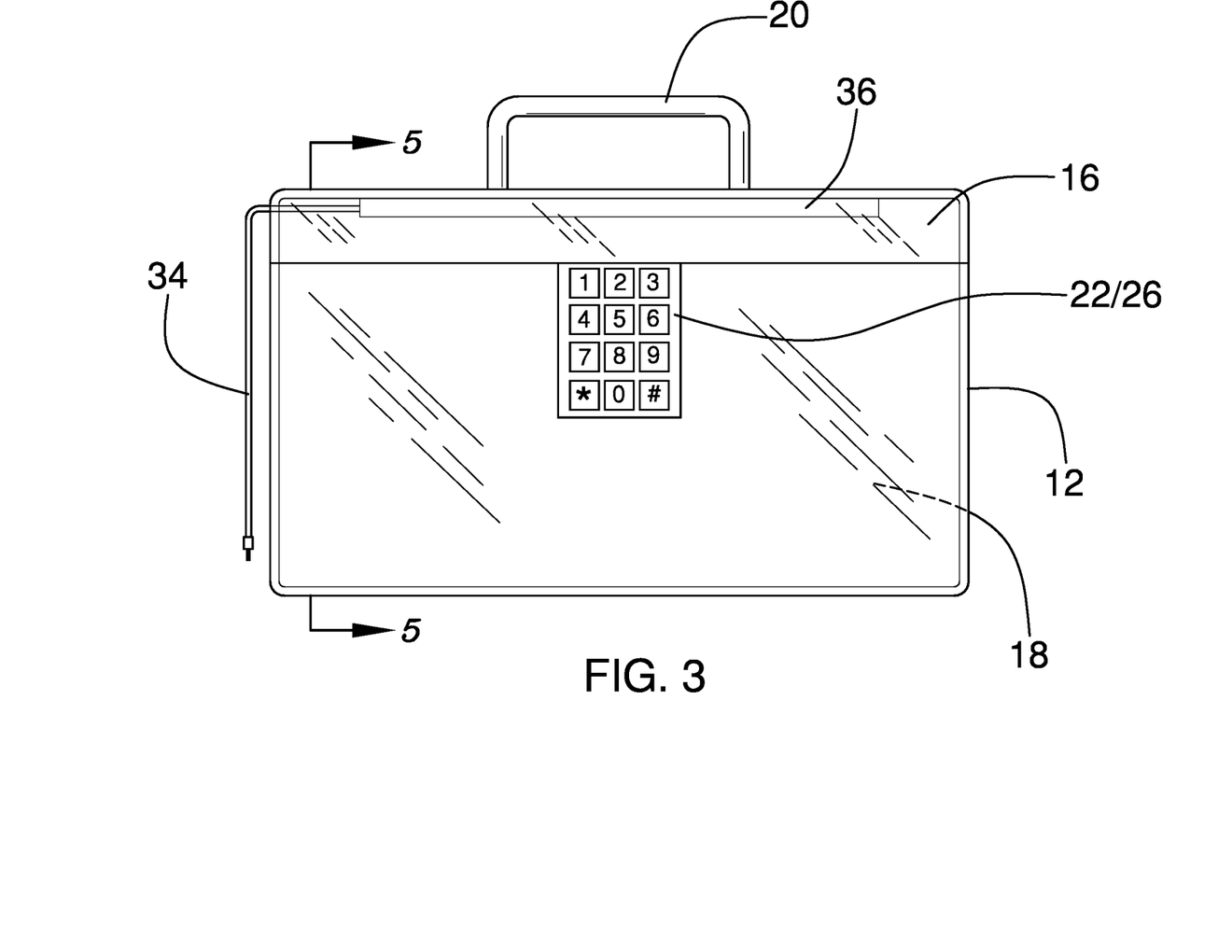
FIG. 3 is a front view of an embodiment of the disclosure.
Figure 4:
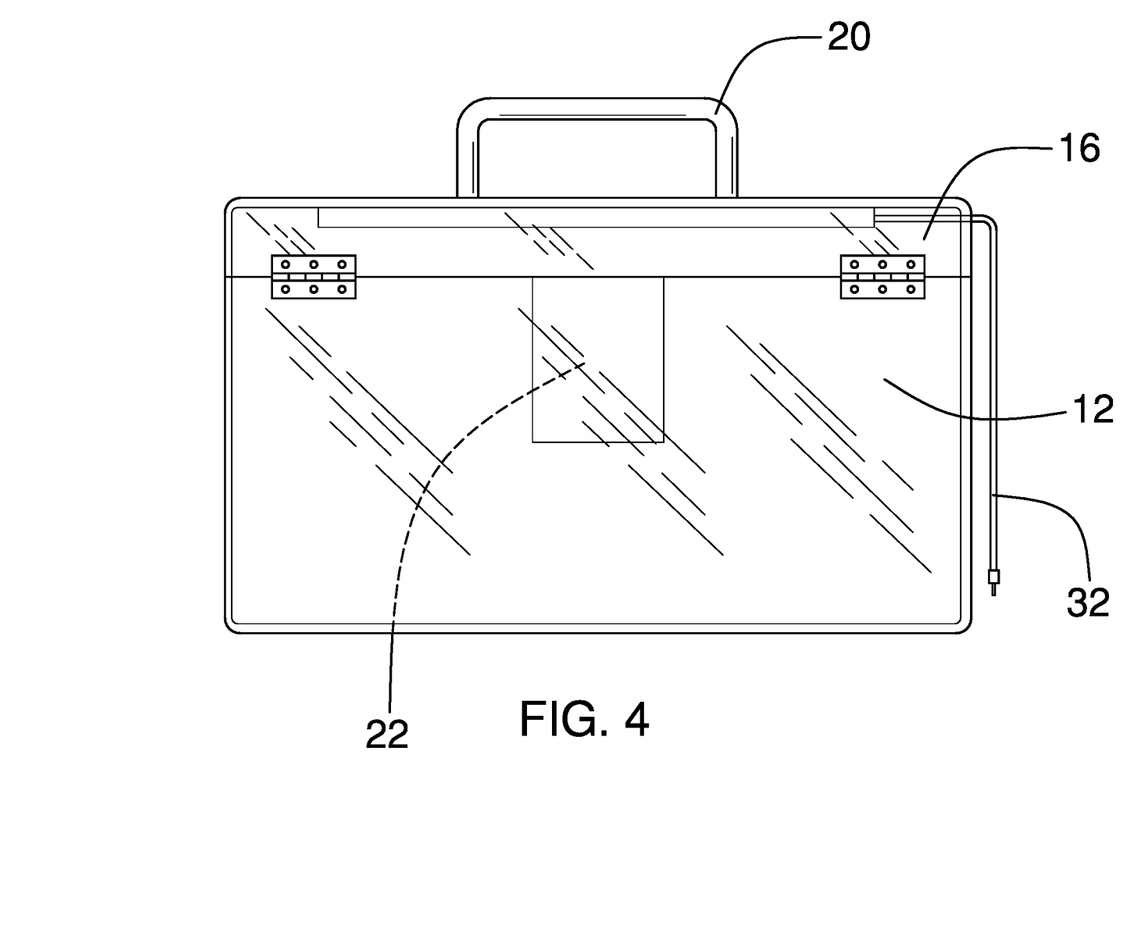
FIG. 4 is a rear view of an embodiment of the disclosure.
Figure 5:
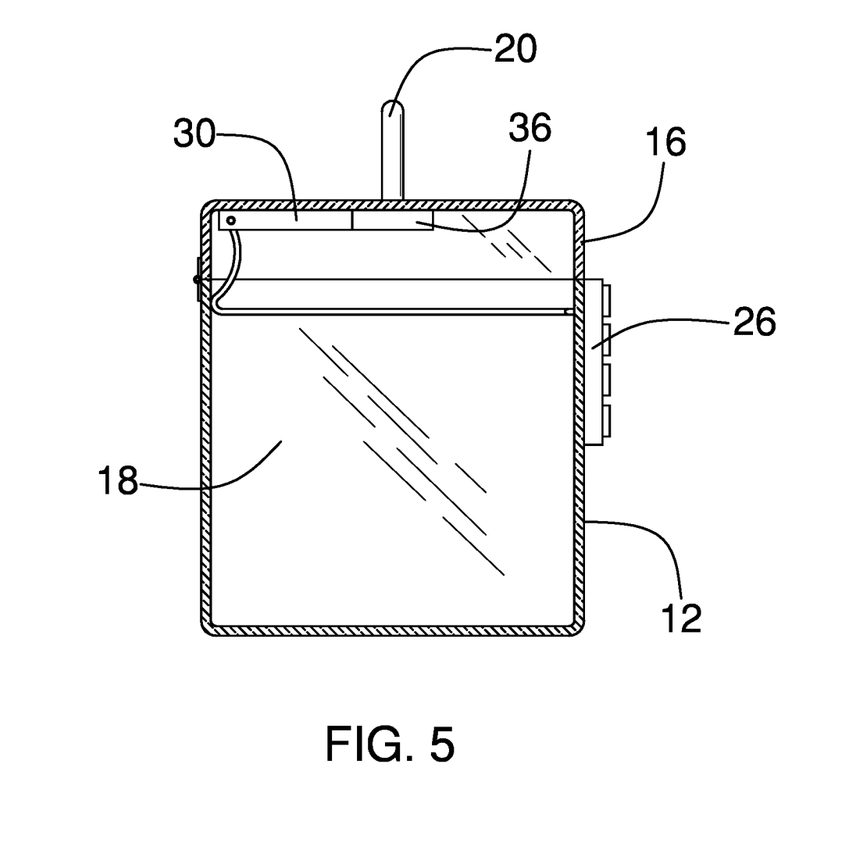
FIG. 5 is a side view of an embodiment of the disclosure.

A battery 30 positioned in the interior space 18 is engaged to one of the box 12 and the lid 16. The battery 30 is operationally engaged to the locking unit 22 to supply power thereto. The battery 30 may be rechargeable. A connector 32 engaged to the battery 30 is configured to selectively engage a charging cord 34. The connector 32 is configured to operationally engage the battery 30 to a source of electrical current to charge the battery 30. As shown in FIG. 2, the connector 32 may comprise the charging cord 34, although the present invention also anticipates a port (not shown) engaged to the box 12 and operationally engaged to the battery 30, to which a cord could be engaged.

The present invention also anticipates a bulb 36 engaged to the lid 16, positioned in the interior space 18, and operationally engaged to the battery 30. The bulb 36 is configured to emit ultraviolet radiation having one or more wavelengths between 200 and 290 nanometers. The bulb 36 thus is configured to disinfect the box 12 and contents thereof. The bulb 36 may comprise low-pressure mercury lamps, excimer (Far-UVC) lamps, pulsed xenon lamps, light-emitting diodes, and the like.

Figure 7:
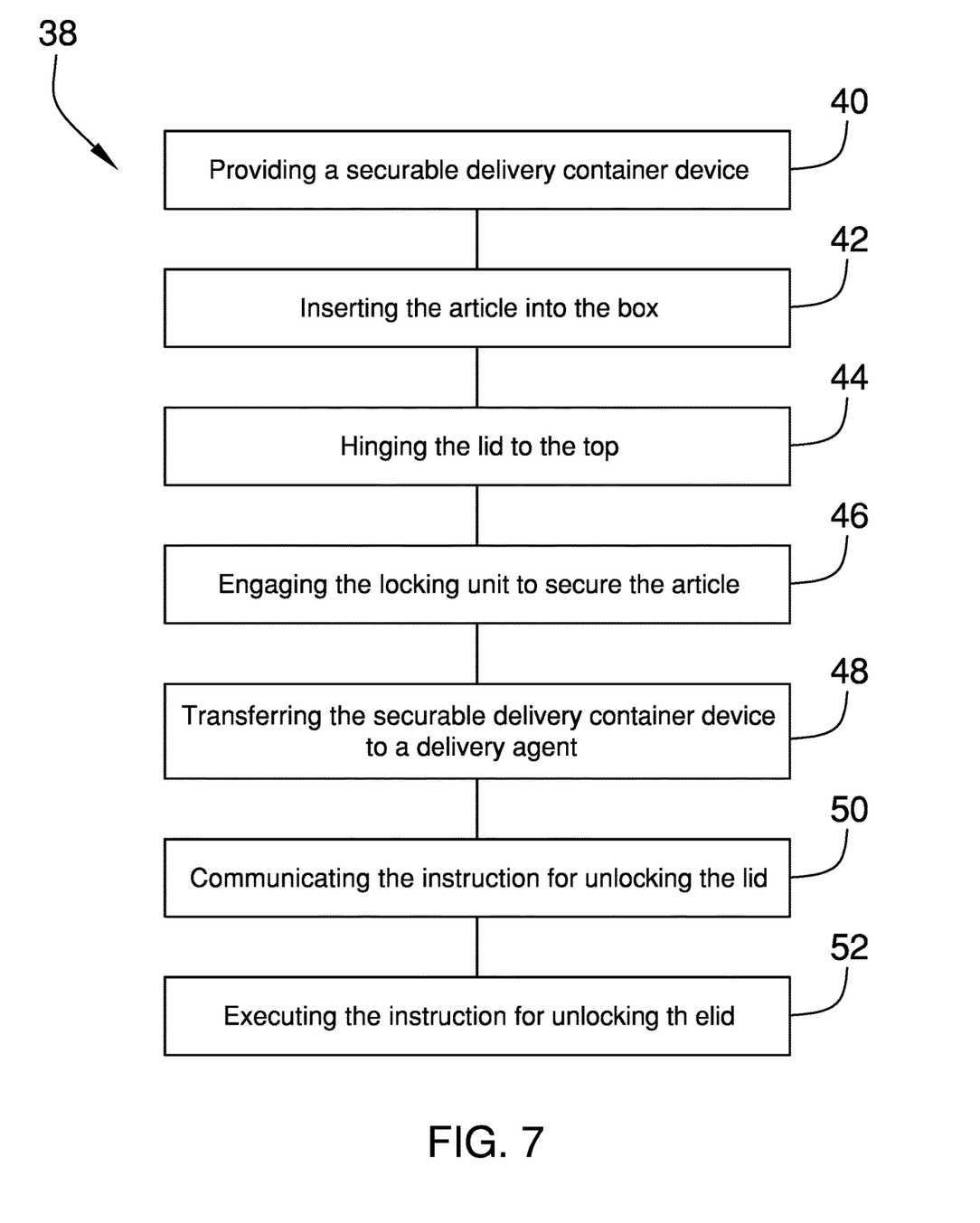
FIG. 7 is a flow diagram of a method utilizing an embodiment of the disclosure.

In use, the device 10 enables a method 38 of securely delivering an article from a sender to an intended recipient. The method 38 comprises a first step 40 of providing a securable delivery container device 10, according to the specification above, for use by the sender. A second step 42 of the method 38 entails inserting the article into the box 12 through the top 14. A third step 44 of the method 38 entails hinging the lid 16 to close the top 14. A fourth step 46 of the method 38 entails engaging the locking unit 22 to secure the article within the interior space 18.

A fifth step 48 of the method 38 entails transferring the securable delivery container device to a delivery agent for delivery to the intended recipient. A sixth step 50 of the method 38 entails generating the instruction 24 for unlocking the lid 16 from the box 12 and communicating it electronically to the intended recipient. A seventh step 52 of the method 38 entails executing the instruction 24 for unlocking the lid 16 from the box 12 and retrieval of the article from the interior space 18 by the intended recipient.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A method of securely delivering an article from a sender to an intended recipient, the method comprising the steps of:
    providing a securable delivery container device for use by the sender, the securable delivery container device comprising:
        a box having a top, the top being open,
        a lid hingedly engaged to the box,
        a locking unit engaged to one of the box and the lid, the locking unit being selectively engageable to the other of the box and the lid, such that the lid is locked to the box in a closed configuration, wherein the box and the lid define an interior space, the locking unit being configured to require an instruction for unlocking the lid from the box, the instruction being electronically communicable between the sender and the intended recipient of the article, and
        a bulb engaged to the lid, positioned in the interior space, and being operationally engaged to the battery, the bulb being configured for emitting ultraviolet radiation having one or more wavelengths between 200 and 290 nanometers;
    inserting the article into the box through the top;
    hinging the lid to close the top;
    engaging the locking unit to secure the article within the interior space;
    transferring the securable delivery container device to a delivery agent for delivery to the intended recipient;
    communicating the instruction for unlocking the lid from the box electronically to the intended recipient;
    executing the instruction for unlocking the lid from the box and retrieving the article from the interior space by the intended recipient; and
    actuating the bulb, wherein the bulb is configured for disinfection of the box and the article.

2. A securable delivery container device comprising:
    a box having a top, the top being open, wherein the box is configured for insertion of an article thereinto through the top;
    a lid hingedly engaged to the box, the lid being positioned for selectively closing the top, such that the box and the lid define an interior space;

a locking unit engaged to one of the box and the lid, the locking unit being selectively engageable to the other of the box and the lid when the lid is positioned in a closed configuration, such that the lid is locked to the box, the locking unit being configured to require an instruction for unlocking the lid from the box, the instruction being electronically communicable between a sender and an intended recipient of the article, wherein the locking unit is configured for securing the article within the interior space until the box is delivered to the intended recipient and the instruction has been executed;

a battery positioned in the interior space and being engaged to one of the box and the lid, the battery being operationally engaged to the locking unit for supplying power thereto; and a bulb engaged to the lid, positioned in the interior space, and being operationally engaged to the battery, the bulb being configured for emitting ultraviolet radiation having one or more wavelengths between 200 and 290 nanometers, wherein the bulb is configured for disinfection of the box and contents thereof.

3. The securable delivery container device of claim 2, wherein the lid and the box comprise plastic.

4. The securable delivery container device of claim 2, wherein the lid and the box are substantially transparent.

5. The securable delivery container device of claim 2, wherein the locking unit comprises a keypad lock, wherein the keypad lock is configured for entry of the instruction, as an alphanumeric code, such that that locking unit is actuated to unlock the lid from the box.

6. The securable delivery container device of claim 2, further including a handle hingedly engaged to the lid, wherein the handle is configured for grasping in a hand of a user, positioning the user for lifting the box and contents thereof.

7. The securable delivery container device of claim 2, further comprising:

the lid and the box comprising plastic, the lid and the box being substantially transparent;

the locking unit comprising a keypad lock, wherein the keypad lock is configured for entry of the instruction, as an alphanumeric code, such that that locking unit is actuated to unlock the lid from the box;

the battery being rechargeable;

a connector engaged to the battery and being configured for selectively engaging a charging cord, wherein the connector is configured for operationally engaging the battery to a source of electrical current for charging the battery; and a handle hingedly engaged to the lid, wherein the handle is configured for grasping in a hand of a user, positioning the user for lifting the box and contents thereof.

8. A securable delivery container device comprising:

a box having a top, the top being open, wherein the box is configured for insertion of an article thereinto through the top;

a lid hingedly engaged to the box, the lid being positioned for selectively closing the top, such that the box and the lid define an interior space;

a locking unit engaged to one of the box and the lid, the locking unit being selectively engageable to the other of the box and the lid when the lid is positioned in a closed configuration, such that the lid is locked to the box, the locking unit being configured to require an instruction for unlocking the lid from the box, the instruction being electronically communicable between a sender and an intended recipient of the article, wherein the locking unit is configured for securing the article within the interior space until the box is delivered to the intended recipient and the instruction has been executed;

a battery positioned in the interior space and being engaged to one of the box and the lid, the battery being operationally engaged to the locking unit for supplying power thereto, the battery being rechargeable; and a connector engaged to the battery and being configured for selectively engaging a charging cord, wherein the connector is configured for operationally engaging the battery to a source of electrical current for charging the battery.

* * * * *